US006818668B2

(12) United States Patent
Roberts

(10) Patent No.: US 6,818,668 B2
(45) Date of Patent: Nov. 16, 2004

(54) 5-ALKYL-7-ALKYLCARBONATE-ISOFLAVONE ESTER AND RELATED METHOD

(75) Inventor: William J. Roberts, Gainesville, FL (US)

(73) Assignee: Biotest Laboratories, LLC, Colorado Springs, CO (US)

( * ) Notice: Subject to any disclaimer, the term of this patent is extended or adjusted under 35 U.S.C. 154(b) by 43 days.

(21) Appl. No.: 10/123,068

(22) Filed: Apr. 12, 2002

(65) Prior Publication Data

US 2003/0195245 A1 Oct. 16, 2003

(51) Int. Cl.$^7$ ...................... A61K 31/35; C07D 311/00; B07D 311/04
(52) U.S. Cl. ...................... 514/456; 514/457; 549/402; 549/403
(58) Field of Search ............................... 514/457, 456; 549/402, 403

(56) References Cited

U.S. PATENT DOCUMENTS

| | | | |
|---|---|---|---|
| 2,843,608 A | 7/1958 | Colton | |
| 3,056,727 A | 10/1962 | Allais et al. | |
| 3,314,856 A | 4/1967 | Allais et al. | |
| 3,433,813 A | 3/1969 | Boswell | |
| 3,435,030 A | 3/1969 | Kilmstra | |
| 3,481,957 A | 12/1969 | Cross et al. | |
| 3,523,126 A | 8/1970 | Boswell | |
| 4,087,524 A | 5/1978 | Grunwell et al. | |
| 4,163,746 A | 8/1979 | Feuer et al. | |
| 4,239,681 A | 12/1980 | Grunwell et al. | |
| 4,841,077 A | 6/1989 | Ito et al. | |
| 5,053,403 A | 10/1991 | Orentreich et al. | |
| 5,247,102 A | 9/1993 | Kallay et al. | |
| 5,387,583 A | 2/1995 | Loria | |
| 5,391,776 A | 2/1995 | Ueno et al. | |
| 5,399,584 A | 3/1995 | Ares et al. | |
| 5,457,103 A | 10/1995 | Rolland et al. | |
| 5,504,105 A | 4/1996 | Chiesi et al. | |
| 5,532,270 A | 7/1996 | Clemente et al. | |
| 5,578,588 A | 11/1996 | Mattern et al. | |
| 5,622,944 A | 4/1997 | Hale et al. | |
| 5,880,117 A | 3/1999 | Arnold | |
| 6,011,027 A | 1/2000 | Arnold | |
| 6,017,964 A | 1/2000 | MacLean et al. | |
| 6,117,429 A | 9/2000 | Bucci | |
| 6,140,469 A | 10/2000 | Shen et al. | |
| 6,455,577 B2 * | 9/2002 | Bok et al. .................. | 549/403 |
| 2001/0041698 A1 | 11/2001 | Arnold | |
| 2001/0056087 A1 | 12/2001 | Arnold | |
| 2002/0183532 A1 | 12/2002 | Roberts | |
| 2003/0134828 A1 | 7/2003 | Roberts | |
| 2003/0134830 A1 | 7/2003 | Roberts | |
| 2003/0134831 A1 | 7/2003 | Roberts | |

FOREIGN PATENT DOCUMENTS

| | | |
|---|---|---|
| BE | 636216 | 8/1963 |
| FR | 1320300 | 3/1963 |
| FR | 1190411 | 2/1974 |
| WO | WO 02/076404 A2 | 10/2002 |

OTHER PUBLICATIONS

Kukla et , Chem. Abs vol. 60 No. 3073, "Insecticidal properties and chemical composition", 1963.*
Itagaki et al, Chem. Abs. vol. 65 No. 408515, "The mess spectra of Chalones, flavones and isoflavones", 1966.*
Fukui et al, Chem. Abs. vol. 59 No. 448229, "Synthesis of 7–hydroxy–2', 4', 5'–trimethoxyisoflavone and related compounds" 1963.*
Kirsch, J., "Flavonoids: The Good, the Bad, and the Ugly," Free Radical and Radiation Biology Program, University of Iowa (Feb. 22, 2001).
Yl et al., "A New Isoflavone from Smilax Glabra", Molecules, vol. 3, 145–147 (1998).
Inaba et al., "Conversion of 4–Androstenediol and 5–Androstenediol to Testosterone, and Conversion of Dehydroepiandrosterone to 4–Androstenediol by Rat Testis In Vitro," Endrocrinol, Japan., 1966, pp. 160–172, 13(2), Japan.
Blaquier et al., "In Vitro Metabolism of Androgens in Whole Human Blood," Acta Endocrinologica, May–Aug. 1967, pp. 697–704, vol. 55, Periodica, Copenhagen, Denmark.
Yamaji et al., "Androstenediol in Canine Spermatic Vein Blood and Its Significance in Testosterone Biosynthesis in Vivo," Endocrinology, 1968, pp. 992–998, vol. 83, USA.
Ohloff et al., "Structural and Configurational Dependence of the Sensory Process in Steroids," Helvetica Chimica Acta, 1983, pp. 192–217, vol. 66.
Franke et al., "Hormonal Doping and Androgenization of Athletes: A Secret Program of the German Democratic Republic Government," Clinical Chemistry, 1997, pp. 1262–1279, vol. 43, No. 7.
Uralets et al., "Over–the–Counter Anabolic Steroids 4–Androsten–3, 17–dione; 4–Androsten–3β, 17β–diol; and 19–nor–4–Androsten–3, 17–dione: Excretion Studies in Men," Journal of Analytical Toxicology, Sep. 1999, pp. 357–366, vol. 23, USA.

(List continued on next page.)

Primary Examiner—D. Margaret Seaman
Assistant Examiner—Raymond Covington
(74) Attorney, Agent, or Firm—Sullivan Law Group

(57) ABSTRACT

A compound is provided for increasing the concentration of a parent isoflavone in a subject in vivo. The parent isoflavone has a skeletal structure including a 5 position and a 7 position, a 5 alkyl group, and a 7-hydroxy group with a 7-hydroxy oxygen appended to the 7 position and a 7-hydroxy hydrogen appended to the 7-hydroxy oxygen. The compound includes a substrate having the skeletal structure of the parent isoflavone, with a 5 position and a 7 position corresponding to the 5 and 7 positions respectively of the parent isoflavone. An alkyl group is appended to the 5 position. A promoiety is appended to the 7-hydroxy oxygen of the substrate as a substitute for the 7-hydroxy hydrogen of the parent isoflavone, the promoiety and the 7-hydroxy oxygen establishing an alkylcarbonate ester. A related method also is provided.

12 Claims, No Drawings

OTHER PUBLICATIONS

Earnest et al., "In Vivo 4–androstene–3,17–dione and 4–androstene–3β, 17β–diol Supplementation in Young Men," European Journal of Applied Physiology, Feb. 2000, pp. 229–232, vol. 81, No. 3, USA.

Lambert, "Rationale and Applications of Lipids as Prodrug Carriers," European Journal of Pharmaceutical Sciences, 2000, pp. S15–S27, vol. 11, Suppl. 2, Elsevier.

Marwah et al., "Ergosteroids IV: Synthesis and Biological Activity of Steroid Glucuronosides Ethers, and Alkylcarbonates," Steroids, 2001, pp. 581–595, vol. 66, Elsevier.

Sylvestre et al., Abstract: "Neighboring–Group Participation of 3.beta.–acetate,–mixed carbonate, or–urethan Groups in Acid–Catalyzed Cleavage of 4.alpha., 5.alpha.–epoxysteroids".

* cited by examiner

5-ALKYL-7-ALKYLCARBONATE-ISOFLAVONE ESTER AND RELATED METHOD

BACKGROUND OF THE INVENTION

1. Field of the Invention

The present invention pertains to the field of biochemistry and more specifically to the field of prodrugs of metabolic agents and related methods.

2. Description of the Related Art

The use of isoflavones as metabolic agents is described in U.S. Pat. No. 4,163,746 to Feuer, assigned to Chinoin Gyogyszer es Vegyeszeti Termekek Gyara Rt. of Hungary ("the Feuer '746 patent"). The Feuer '746 patent identifies a class of isoflavones characterized as possessing a methyl group at the 5-carbon position and a hydroxyl or ether group at the 7 carbon position. The Feuer '746 patent lists 5-methyl-7-methoxy-isoflavone, 5-methyl-7-ethoxy-isoflavone, 5-methyl-7-(2-hydroxy-ethoxy)-isoflavone, and 5-methyl-7-isopropoxy-isoflavone as preferred isoflavones.

The Feuer '746 patent purports that its class of isoflavones were shown to have utility in promoting anabolic activity and increasing calcium, phosphorous, potassium, and nitrogen retention to a significant degree. The list of preferred isoflavones mentioned above also is purported to produce a significant weight gain increase in domestic animals, with the weight surplus consisting of meat, rather than fat. According to the Feuer '746 patent, perhaps the most significant advantage of its class of isoflavones over conventional anabolic agents was that its isoflavones did not produce androgenic or liver damaging side effects. Due to its anabolic properties, the isoflavones of the Feuer '746 patent are described as having utility in the treatment of diseases, and particular utility in the treatment of osteoporosis of gerontological and immobilation origin.

Without necessarily wishing to be bound by any theory, it is believed that the isoflavones described in the Feurer '746 patent, such as 5-methyl- 7-methoxy-isoflavone, are prodrugs, that is, a compound that itself has no anabolic activity but, when administered in the body, is metabolized or converted into a natural or desired form, 7-hydroxy-5-methyl-isoflavone, which promotes anabolic activity. Thus, such prodrugs, i.e., 5-methyl-7-methoxy-isoflavone, become substrates for in vivo bioconversion into the desired parent compounds. (Incidentally, if 7-hydrox-5-methyl-isoflavone were administered directly, i.e., not in a prodrug state, the liver would likely metabolize substantially all of the 7-hydroxy-5-methyl-isoflavone during the first pass.)

Based on findings of the Feuer '746 patent and other reported research, the compound 5-methyl-7-methoxy-isoflavone is commercially sold as a nutritional supplement and advertised as an anabolic agent for promoting muscle mass gains and body fat composition losses, while not causing adverse side effects associated with the use of steroids.

However, the effectiveness of the prodrug 5-methyl-7-methoxy isoflavone has been limited due to difficulties that the human body encounters in converting the prodrug to its parent isoflavone in vivo. In some instances, its conversion into the desired parent compound, 7-hydroxy-5-methyl-isoflavone, is limited, for example, because it is removed from the system through the "first pass effect," wherein the compound is metabolized by the liver prior to reaching general circulation. A large proportion of the prodrug also either does not undergo conversion or converts into undesirable products. It is estimated that approximately 50% of the prodrug 5-methyl-7-methoxy isoflavone administered to a human is converted in vivo to 7-hydroxy-5-methyl-isoflavone. Even where the desired bioconversion occurs, the rate of conversion can be sufficiently low that undesirably large quantities of the prodrug must be taken to achieve desired effects. This itself can have undesirable side effects.

It is advantageous in many instances to have a prodrug that may be administered in a convenient form, such as by oral, or sublingual administration. Many prodrugs have not been amenable to such administration, however, because they tend to be broken down prior to absorption in vivo when administered in this fashion.

OBJECTS OF THE INVENTION

Accordingly, an object of the present invention is to provide compositions and methods that can be used to increase the in vivo concentration and bioavailability of the parent compound, 5-alkyl-7-hydroxy-isoflavone.

Another object of the invention according to certain aspects is to provide compounds and methods that can be used to increase the in vivo concentration and bioavailability of a parent 5-alkyl-7-hydroxy-isoflavone while being amenable to convenient administration, such as by oral, or sublingual administration.

Additional objects and advantages of the invention will be set forth in the description that follows, and in part will be apparent from the description, or may be learned by practice of the invention. The objects and advantages of the invention may be realized and obtained by means of the instrumentalities and combinations pointed out in the appended claims.

SUMMARY OF THE INVENTION

To achieve the foregoing objects, and in accordance with the purposes of the invention as embodied and broadly described in this document, a compound comprising an alkylcarbonate ester is provided. The compound represented by the formula I

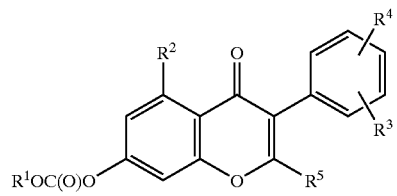

wherein $R^1$ consists of a member selected from the group consisting of a straight-chain, branched, and cyclic alkyl; $R^2$ consists of a member selected from the group consisting of a straight-chain, branched, and cyclic alkyl; $R^3$ and $R^4$ are the same or different, and selected from the group consisting of hydrogen, alkyl, hydroxy, and alkyoxy; and $R^5$ consists of a member selected from the group consisting of hydrogen and an alkyl.

The alkylcarbonate ester optionally but preferably has an alkyl chain length of not more than 12, and more preferably of less than 11. The alkylcarbonate ester may consists of a member selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl carbonate, cyclopentylmethyl carbonate, cyclopentylpropyl carbonate, cyclohexylmethyl carbonate, cyclohexylpropyl carbonate, and mixtures thereof. Alkyl carbonate esters having lower carbon chain lengths generally are preferred, although not universally so. The ethyl carbonate is a preferred form of the alkylcarbonate in the molecule. The compound itself according to this aspect of the invention may assume a number of specific forms. It may, for example, comprise 5-methyl-7-ethylcarbonate-isoflavone. It also may take the form of mixtures or combinations of compounds.

In accordance with a preferred variation of the first aspect of the invention, the compound has the following formula II

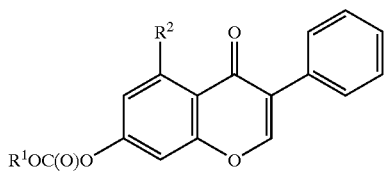

wherein $R^1$ consists of a member selected from the group consisting of a straight-chain, branched, and cyclic alkyl; and $R^2$ consists of a member selected from the group consisting of a straight-chain, branched, and cyclic alkyl.

In accordance with a second aspect of the invention, a compound is provided for increasing the concentration of a parent isoflavone in a subject in vivo. The parent isoflavone has a skeletal structure including a 5 position and a 7 position and the parent isoflavone further has a 5 alkyl group, and a 7-hydroxy group comprising a 7-hydroxy oxygen appended to the 7 position and a 7-hydroxy hydrogen appended to the 7-hydroxy oxygen.

The compound of the second aspect of the invention comprises a substrate having the skeletal structure of the parent isoflavone. The substrate comprises a 5 position and a 7 position corresponding to the 5 and 7 positions respectively of the parent isoflavone. A straight-chain, branched, or cyclic alkyl group is appended to the 5 position. A promoiety is appended to the 7-hydroxy oxygen of the substrate as a substitute for the 7-hydroxy hydrogen of the parent isoflavone, the promoiety and the 7-hydroxy oxygen establishing an alkylcarbonate ester.

The substrate has the skeletal structure of the parent isoflavone, which is preferably 7-hydroxy-5-alkyl-isoflavone, and more preferably 7-hydroxy-5-methyl-isoflavone.

The alkylcarbonate ester may be as described above. For example, the alkylcarbonate ester optionally but preferably has a maximum alkyl chain length of 12 carbon atoms, and more preferably of less than 11 carbon atoms. The alkylcarbonate may, for example, be selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentylmethyl carbonate, cyclopentyl carbonate, cyclopentylpropyl carbonate, cyclohexylmethyl carbonate, cyclohexylpropyl carbonate, and mixtures thereof. Alkyl carbonate esters having lower carbon chain lengths generally are preferred, although not universally so. Ethyl carbonate is a preferred form of the alkylcarbonate in the compound. The compound itself according to this aspect of the invention may assume a number of specific forms. It may, for example, comprise 5-methyl-7-ethylcarbonate-isoflavone. It also may take the form of mixtures or combinations of compounds.

In accordance with a third aspect of the invention, a method is provided for increasing the concentration of a parent isoflavone in a subject in vivo, the parent isoflavone having a skeletal structure including a 5 position and a 7 position and the parent isoflavone further having a 5 alkyl group, and a 7-hydroxy group comprising a 7-hydroxy oxygen appended to the 7 position and a 7-hydroxy hydrogen appended to the 7-hydroxy oxygen.

The method according to this third aspect of the invention comprises administering to the subject a compound comprising a substrate and a promoiety. The compound has the general formula I

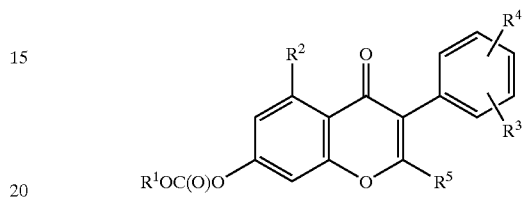

wherein $R^1$ consists of a member selected from the group consisting of a straight-chain, branched, and cyclic alkyl; R2 consists of a member selected from the group consisting of a straight-chain, branched, and cyclic alkyl; $R^3$ and $R^4$ are the same or different, and selected from the group consisting of hydrogen, alkyl, hydroxy, and alkyoxy; and $R^5$ consists of a member selected from the group consisting of hydrogen and an alkyl.

The method of this third aspect of the invention further comprises converting the compound in vivo into the parent isoflavone. The subject may be a human being, in which case the in vivo conversion comprises converting the compound into the parent isoflavone in vivo within the human being.

In accordance with a preferred variation of the third aspect of the invention, the compound has the following formula II

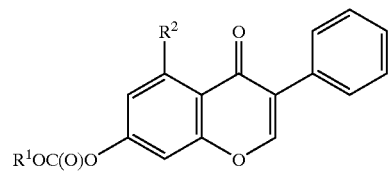

wherein $R^1$ consists of a member selected from the group consisting of a straight-chain, branched, and cyclic alkyl; and $R^2$ consists of a member selected from the group consisting of a straight-chain, branched, and cyclic alkyl.

In accordance with a fourth aspect of the invention, a method is provided for increasing the concentration of a parent isoflavone in a subject in vivo, the parent isoflavone having a skeletal structure including a 5 position and a 7 position and the parent isoflavone further having a 5 alkyl group, and a 7-hydroxy group comprising a 7-hydroxy oxygen appended to the 7 position and a 7-hydroxy hydrogen appended to the 7-hydroxy oxygen.

According to this fourth aspect of the invention, a subject is administered a compound comprising a substrate and a promoiety. The substrate has the skeletal structure of the parent isoflavone comprising a 5 position, and a 7 position corresponding to the 5 and 7 positions respectively of the parent isoflavone. The 5 position has an alkyl substituent appended thereto. The promoiety is appended to the 7-hydroxy oxygen of the substrate as a substitute for the 7-hydroxy hydrogen of the parent isoflavone. The promoiety and the 7-hydroxy oxygen establish an alkylcarbonate ester. The compound is converted in vivo into the parent isoflavone.

The alkylcarbonate ester of the third and fourth aspects of the invention may be as described above. In accordance with the third and fourth aspects of the invention, the compound administration may comprise peroral administration, transdermal administration, sublingual administration, and other means. Peroral administration is presently preferred.

DETAILED DESCRIPTION OF THE PREFERRED EMBODIMENTS AND METHODS

Reference will now be made in detail to the presently preferred embodiments and methods of the invention. It should be noted, however, that the invention in its broader aspects is not limited to the specific details, representative compositions and methods, and illustrative examples described in this section in connection with the preferred embodiments and methods. The invention according to its various aspects is particularly pointed out and distinctly claimed in the attached claims read in view of this specification, and appropriate equivalents.

It is to be noted that, as used in the specification and the appended claims, the singular forms "a," "an," and "the" include plural referents unless the context clearly dictates otherwise.

In accordance with one aspect of the invention, a compound comprising an alkylcarbonate ester, represented by the general formula (I) below is provided:

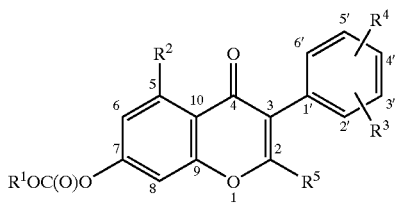

This numbering above on formula (I) for the ring identification and carbon numbering system are well known in the field of chemistry. In a preferred embodiment of the invention, $R^2$ is a short-chain alkyl, preferably methyl. In an especially preferred embodiment of the invention, $R^2$ is methyl and $R^3$, $R^4$, and $R^5$ are hydrogen. Generally, $R^3$, $R^4$ and $R^5$ can append off of any of C2' to C6'. Further, $R^3$ and $R^4$ may be the same or different, and can be selected from the group consisting of hydrogen, alkyl, hydroxy, and alkoxy.

The compound preferably but optionally is for treatment of a human being to supplement or increase the concentration of the preferred parent isoflavone, i.e., 7-hydroxy-5-alkyl-isoflavone, in vivo. The compound is most preferably designed for use as a muscle mass enhancement agent, although other uses, such as for osteoporosis, may be possible. This is not necessarily limiting, however, and veterinary applications also are possible in certain instances.

In accordance with an especially preferred embodiment of the invention, the compound comprises a substrate and a promoiety, with the substrate having the skeletal structure of the parent isoflavone, which is preferably 7-hydroxy-5-methyl isoflavone.

The promoiety is appended to the 7-hydroxy oxygen of the substrate as a substitute for the 7-hydroxy hydrogen. It comprises and preferably consists of an alkylcarbonate ester. The alkyl group may be linear, branched, cyclical, etc. The promoiety preferably but optionally has an alkyl chain length (counting only the carbon atoms) of not more than 12, and more preferably of less than 11. The alkylcarbonate ester may be selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl methyl carbonate, cyclopentylpropyl carbonate, cyclohexyl methyl carbonate, cyclohexylpropyl carbonate, and mixtures thereof. Other alkyl carbonate esters, however, may be used. Alkyl carbonate esters having lower carbon chain lengths generally are preferred, although not universally so. Ethylcarbonate esters generally are even more preferred.

The compound according to this aspect of the invention in its presently preferred embodiments may comprise 5-methyl-7-ethylcarbonate-isoflavone ester, 5-methyl-7-methylcarbonate-isoflavone ester, and mixtures thereof The method according to this aspect of the invention comprises administering to the subject a compound comprising a substrate and a promojety. The substrate has the skeletal structure of the parent isoflavone comprising a 5 position and a 7 position corresponding to the 5 and 7 positions respectively of the parent isoflavone. The promoiety is appended to the 7 position of the substrate as a substitute for the 7-hydroxy hydrogen of the parent isoflavone, and comprises an alkylcarbonate ester. The method further comprises converting the compound in vivo into the parent isoflavone. The subject again preferably but optionally is a human being, and the in vivo conversion thus correspondingly comprises converting the compound into the parent isoflavone in vivo within the human being.

In each of the aforementioned methods, the compound administration may comprise peroral administration, transdermal administration, sublingual administration, and other means. The administration of the compound also may be by combinations of these techniques or approaches. Peroral administration is presently preferred.

The compound may be contained or encapsulated by an enteric coating. In some forms, particularly those intended for peroral administration, it is preferable albeit optional for the compound to include a carrier. The carrier may be a solid, a liquid, a semi-solid, liquid or other suitable form. A preferred liquid carrier is an aqueous emulsion including purified water, glycerin, polysorbate, lecithin, natural flavor blend, methylparaben, propylparaben, sodium benzoate, EDTA, and vegetable gum. Another preferred aqueous emulsion comprises fatty acid ethyl esters, polysorbate 60, lecithin, and cholesterol or an oil. Still another preferred liquid carrier comprises water, glycerin, polysorbate, lecithin, sodium benzoate, ethylene diamine tetraacetic acid ("EDTA"), potassium sorbate, grapefruit seed extract, and vegetable gum. These liquid carriers are particularly applicable if administered sublingually.

When administered orally or sublingually, the compound enters the gastrointestinal ("GI") tract, and ultimately the blood stream. Through more direct methods such as through transdermal, the compound enters directly into the blood stream. In each of the instances, the compound may react to form the parent isoflavone or a prodrug of the parent isoflavone.

One limitation of known prodrugs is that, once they are transformed into the parent drug, they are broken down in the body, and particularly in the liver. This breakdown reduces in vivo concentration and bioavailability of the drug. This breakdown effect has been observed with 5-methyl-7-methoxy-isoflavone. In the presently preferred embodiments of the invention, however, the compounds are less prone to such breakdown in the body relative to many known prodrug-type compounds. This in many instances is attributable to the alkylcarbonate ester promoiety, which makes the compound more resistant to hydrolysis and other reactions that inhibit or destroy them in the body. In vivo concentrations thus can be maintained more readily, and bioavailability of the parent isoflavone can be improved. It has been estimated that the duration of action for 5-methyl-7-ethylcarbonate-isoflavone may be twice that of 5-methyl-7-methoxy-isoflavone.

The compound preferably is administered in amounts effective to supplement or increase the concentration of the parent isoflavone in vivo. According to a related aspect of the method, the compound may be administered using a dosage given periodically for a maximum of four weeks, followed by a period, for example, of at least two weeks, of non-administration. This can permit the compound to supplement or increase the concentration of the parent isoflavone in vivo for an effective period, and then terminate further dosages of the compound as its effectiveness attenuates.

In accordance with presently preferred versions of the inventive method, the compound administration, particularly when applied to humans, comprises administering the compound in an amount ranging from 1.0 mg to 1 gram per day, more preferably in an amount ranging from 50 mg to 500 mg twice per day, and even more preferably in an amount ranging from 300 mg to 400 mg twice per day, most preferably 375 mg twice per day. Preferably, two daily servings are taken 8 to 10 hours apart with food.

The 5-alkyl-7-alkylcarbonate-isoflavone may be prepared in accordance with known procedures used to synthesize alkylcarbonate esters. By way of example, 7-hydroxy-5-methyl-isoflavone may be reacted in pyridine with 1 to 1.5 equivalent of ethyl chloroformate added dropwise to prepare 5-methyl-7-ethylcarbonate-isoflavone. Care should be taken to avoid excessively rapid generation of heat from the resulting exothermic reaction. Suitable solvents in which the reaction may be carried out include pyridine, which may be present in an amount of, for example, 70-140 ml per 1.0 gram of 7-hydroxy-5-methyl-isoflavone, with the reaction proceeding over a 24-hour period with stirring. The solution may then be filtered, washed (for example, in a separatory funnel with acidic water, once with neutral water), then dried over sodium sulfate.

The preparation of 7-hydroxy-5-alkyl-isoflavones and 7-alkoxy-5-alkyl-isoflavones is known in the art. Several preparatory processes that may be used are disclosed in the Feuer '746 patent.

Additional advantages and modifications will readily occur to those skilled in the art. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

What is claimed is:

1. A compound comprising an alkylcarbonate ester, the compound represented by the formula

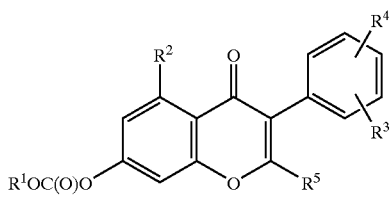

wherein $R^1$ consists of a member selected from the group consisting of a straight-chain, branched, and cyclic alkyl;

$R^2$ consists of a member selected from the group consisting of a straight-chain, branched, and cyclic alkyl;

$R^3$ and $R^4$ are the same or different, and selected from the group consisting of hydrogen, alkyl, hydroxy, and alkyoxy; and $R^5$ consists of a member selected from the group consisting of hydrogen and an alkyl.

2. A compound as set forth in claim 1, wherein $R^1$ has a maximum of 12 carbon atoms.

3. A compound as set forth in claim 1, wherein the alkylcarbonate ester consists of a member selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl methyl carbonate, cyclopentylpropyl carbonate, cyclohexyl methyl carbonate, and cyclohexylpropyl carbonate.

4. A compound as set forth in claim 1, wherein the alkylcarbonate ester consists of ethyl carbonate.

5. A compound as set forth in claim 1, wherein $R^2$ consists of methyl.

6. A compound comprising an alkylcarbonate ester, the compound represented by the formula

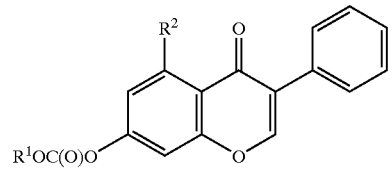

wherein $R^1$ consists of a member selected from the group consisting of a straight-chain, branched, and cyclic alkyl; and $R^2$ consists of a member selected from the group consisting of a straight-chain, branched, and cyclic alkyl.

7. A compound as set forth in claim 6, wherein $R^1$ has a maximum of 12 carbon atoms.

8. A compound as set forth in claim 6, wherein the alkylcarbonate ester consists of a member selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl methyl carbonate, cyclopentylpropyl carbonate, cyclohexyl methyl carbonate, and cyclohexylpropyl carbonate.

9. A compound as set forth in claim 6, wherein the alkylcarbonate ester consists of ethyl carbonate.

10. A compound as set forth in claim 6, wherein $R^2$ consists of methyl.

11. A compound as set forth in claim 6, wherein the alkylcarbonate consists of ethyl carbonate, and wherein $R^2$ consists of methyl.

12. A compound as set forth in claim 6, wherein the alkylcarbonate consists of methyl carbonate, and wherein $R^2$ consists of methyl.

* * * * *